(12) United States Patent
Wynn

(10) Patent No.: US 8,250,937 B2
(45) Date of Patent: Aug. 28, 2012

(54) ASEPTIC MANIFOLD AND PROBE ASSEMBLY

(75) Inventor: William H. Wynn, Hillsborough, CA (US)

(73) Assignee: ASEPCO, Mountain View, CA (US)

( * ) Notice: Subject to any disclaimer, the term of this patent is extended or adjusted under 35 U.S.C. 154(b) by 295 days.

(21) Appl. No.: 12/721,060

(22) Filed: Mar. 10, 2010

(65) Prior Publication Data

US 2011/0223076 A1 Sep. 15, 2011

(51) Int. Cl.
*G01D 21/00* (2006.01)
*G01N 11/00* (2006.01)
*G01N 25/00* (2006.01)

(52) U.S. Cl. ............... 73/866.5; 73/61.74; 73/61.46; 73/61.47; 422/500; 422/544; 422/545; 422/546; 422/83

(58) Field of Classification Search .................. 422/310, 422/286, 544–545, 500, 547, 552, 83, 105, 422/546; 73/866.5, 61.74, 61.46, 61.47
See application file for complete search history.

(56) References Cited

U.S. PATENT DOCUMENTS

| | | | | |
|---|---|---|---|---|
| 4,159,304 A | * | 6/1979 | Shono | 422/562 |
| 4,315,990 A | * | 2/1982 | Sheets | 435/287.1 |
| 4,323,440 A | * | 4/1982 | Akatsuka | 204/428 |
| 4,652,849 A | * | 3/1987 | Matsuura et al. | 338/34 |
| 4,754,771 A | * | 7/1988 | Tangherlini et al. | 134/102.1 |
| 5,739,441 A | * | 4/1998 | Friese et al. | 73/866.5 |
| 7,661,328 B2 | * | 2/2010 | Janz et al. | 73/866.5 |
| 2005/0155408 A1 | * | 7/2005 | Weyl et al. | 73/23.31 |

* cited by examiner

*Primary Examiner* — Brian R Gordon
(74) *Attorney, Agent, or Firm* — Edward S. Wright

(57) ABSTRACT

Manifold and probe assembly for use a bioprocessing vessel. The manifold has a chamber which communicates with the interior of the vessel and a plurality of ports which communicate with the chamber. Elongated sensing probes are threadedly connected to the ports with end portions of the probes extending into the chamber. Gaskets having generally annular bodies with conically inclined beveled faces are mounted on the end portions of the probes, with the beveled faces engaging conically inclined surfaces of seats in the ports and the gaskets being axially compressed and radially expanded into sealing engagement with the probes. The seating surfaces have inner and outer sections with different angles of inclination which produce greater radial expansion and tighter sealing with the probes. The probes are carried by adapter sleeves which are threadedly connected to the ports, with thrust washers between the distal ends of the sleeves and the gaskets for protecting the gaskets while the sleeves are being connected to the ports and the gaskets are being compressed. Stops limit the travel of the sleeves and control the degree to which the gaskets are compressed.

26 Claims, 5 Drawing Sheets

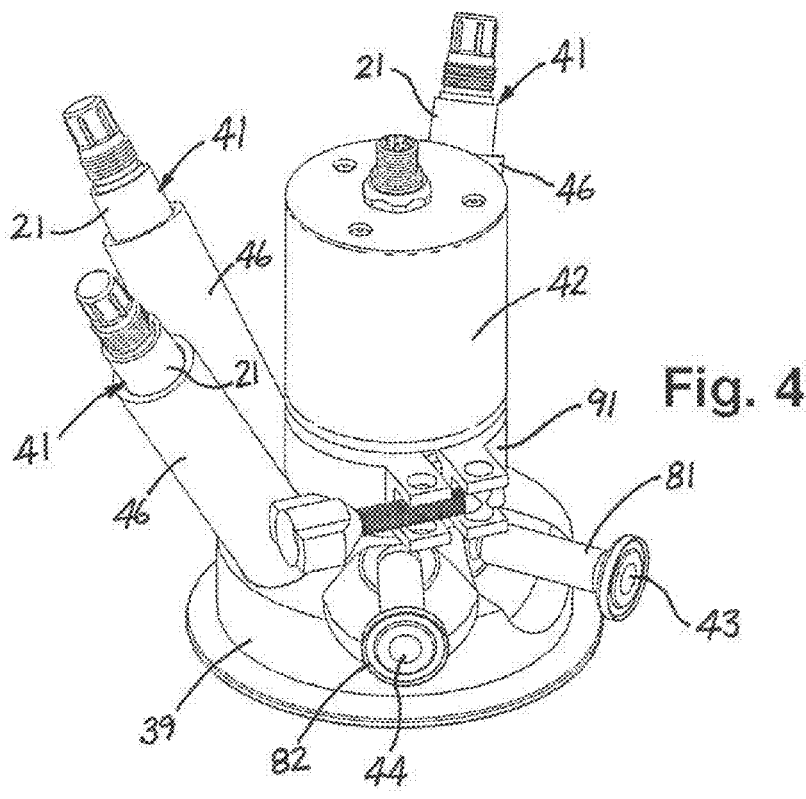
Fig. 4
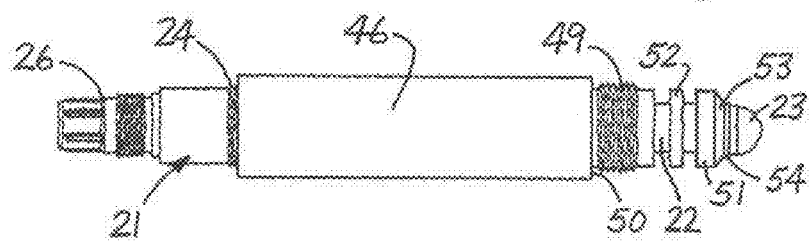
Fig. 5
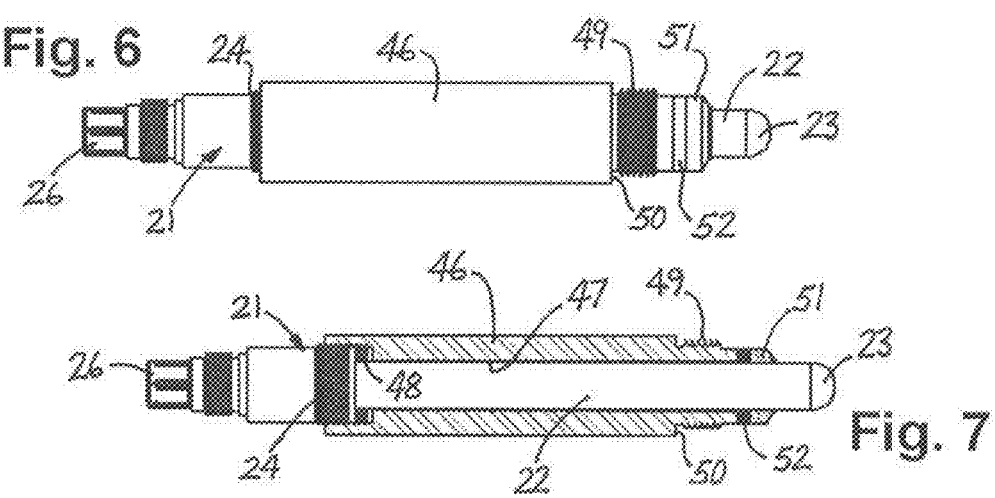
Fig. 6
Fig. 7

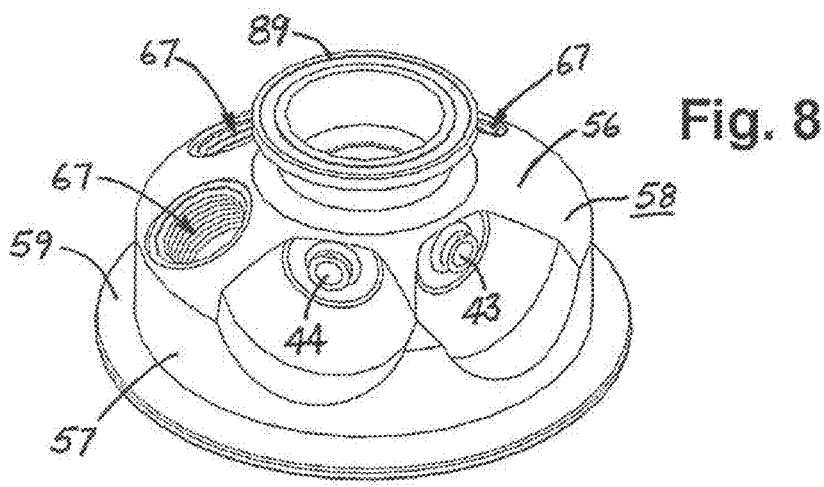
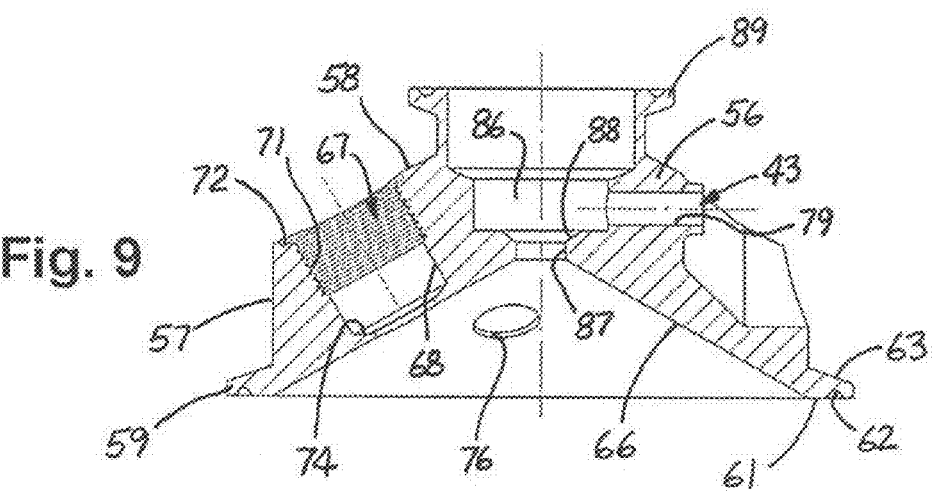
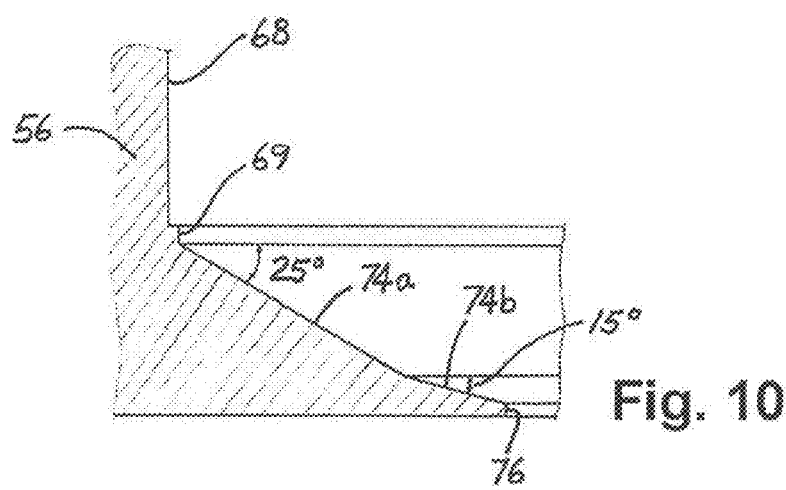

ASEPTIC MANIFOLD AND PROBE ASSEMBLY

BACKGROUND OF THE INVENTION

1. Field of Invention

This invention pertains generally to the monitoring of parameters in bioprocesses and, more particularly, to an aseptic manifold and probe assembly for use on a vessel in which a bioprocess is carried out.

2. Related Art

In bioprocessing, parameters such as conductivity, pH, temperature, oxidation reduction potential, O2, CO2, and optical density are commonly monitored with probes which are inserted into the vessels in which the processes are carried out.

A typical probe of the type currently in use and a typical installation of such a probe are illustrated in FIGS. 1-3. The probe 21 has an elongated body 22 with a dome-shaped tip 23 at one end, an enlarged threaded section 24 toward the other end, and an electrical connector 26 at the end opposite the tip. The probe is mounted in an adapter 27 which is mounted in a fitting 28 welded to the side wall 29 of a vessel, with the tip of the probe immersed in the fluid in the vessel.

The adapter has an axially extending bore 31 with an internally threaded section 32 corresponding to the threaded section of the probe. When the probe is threaded into the adapter, the body of the probe extends through the bore and beyond the distal end of the adapter, with O-rings 33, 33 providing a seal between the adapter and the probe. The adapter also has a radially extending external flange 34 which is engaged by a retaining nut 36 to secure the adapter and the probe to the fitting. An O-ring 37 provides a seal between the adapter and the fitting.

This installation has a number of limitations and disadvantages. The port fitting is welded on both sides of the vessel wall and is inclined at an angle of approximately 15 degrees to the horizontal. Both welds must be ground and polished, and the orientation of the port must be maintained. These are labor intensive operations which must be repeated for each probe that is used. Moreover, during the welding operations, the fittings and vessel wall can overheat and warp, and the fitting threads can be damaged. With inclined fittings and O-ring seals, the gasket seats are set in such a way that sterilization can be difficult, and visual inspection of the seal areas to ensure they are clean and free of residue is almost impossible.

OBJECTS AND SUMMARY OF THE INVENTION

It is, in general, an object of the invention to provide a new and improved manifold and probe assembly for use on a vessel in which a bioprocess is carried out.

Another object of the invention is to provide a manifold and probe assembly of the above character which overcomes the limitations and disadvantages of the prior art.

These and other objects are achieved in accordance with the invention by providing a manifold having a chamber which communicates with the interior of a bioprocessing vessel and a plurality of ports which communicate with the chamber, elongated sensing probes threadedly connected to the ports with end portions of the probes extending into the chamber, gaskets having generally annular bodies with conically inclined beveled faces mounted on the end portions of the probes, and seats in the ports with conically inclined surfaces engaged by the beveled faces, with the gaskets being axially compressed and radially expanded into sealing engagement with the probes. The seating surfaces have inner and outer sections with different angles of inclination which produce greater radial expansion and tighter sealing with the probes. The probes are carried by adapter sleeves which are threadedly connected to the ports, with thrust washers between the distal ends of the sleeves and the gaskets for protecting the gaskets while the sleeves are being connected to the ports and the gaskets are being compressed. Stops limit the travel of the sleeves and control the degree to which the gaskets are compressed.

BRIEF DESCRIPTION OF THE DRAWINGS

FIG. 4 is an isometric view of one embodiment of a manifold and probe assembly according to the invention.

FIG. 5 is a side elevational view, partly exploded, of one of the probe and sleeve assemblies in the embodiment of FIG. 4.

FIG. 6 is a side elevational view of the probe and sleeve assembly of FIG. 4, fully assembled.

FIG. 7 is a centerline sectional view of the probe and sleeve assembly of FIG. 6.

FIG. 8 is an isometric view of the manifold in the embodiment of FIG. 4.

FIG. 9 is a centerline sectional view of the manifold in the embodiment of FIG. 4.

FIG. 10 is an enlarged, fragmentary sectional view of the seating area of one of the probe ports in the manifold in the embodiment of FIG. 4, rotated to a vertical position.

DETAILED DESCRIPTION

Figure 1:
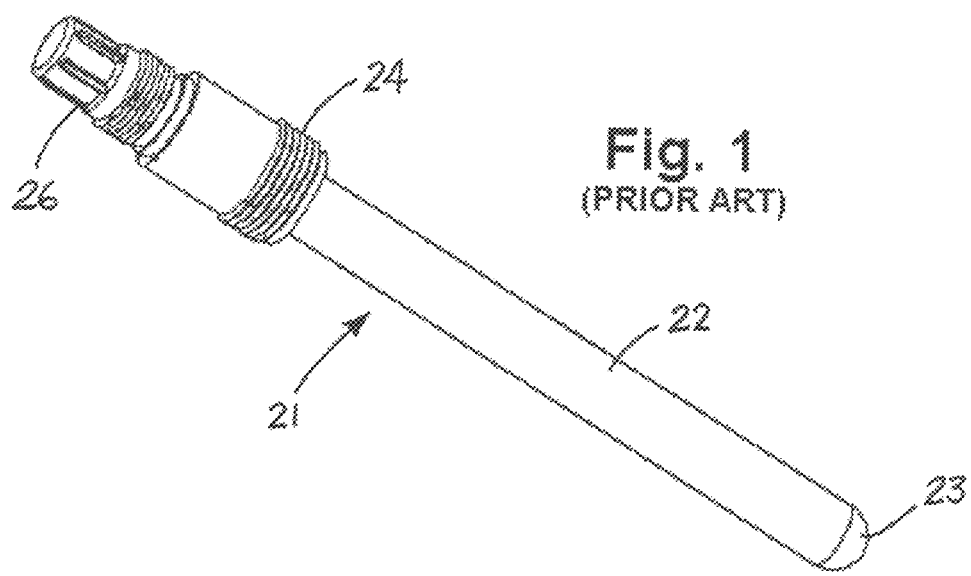
FIG. 1 is an isometric view of an existing probe for monitoring conditions in bioprocesses.
Figure 2:
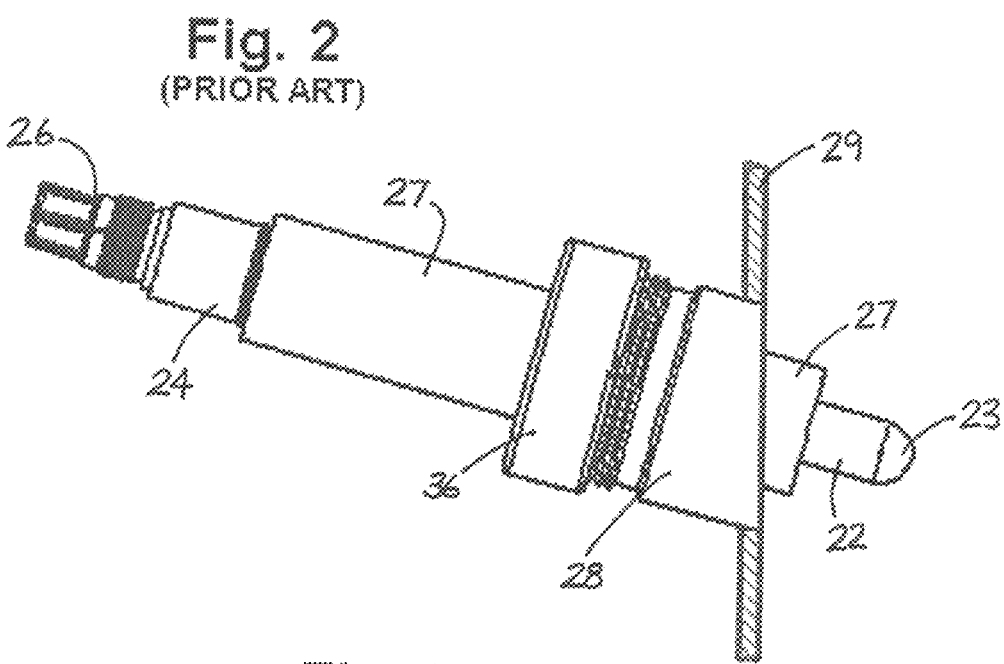
FIG. 2 is a side elevational view illustrating the manner in which the probe of FIG. 1 is commonly installed on the wall of a vessel in which a bioprocess is carried out.
Figure 3:
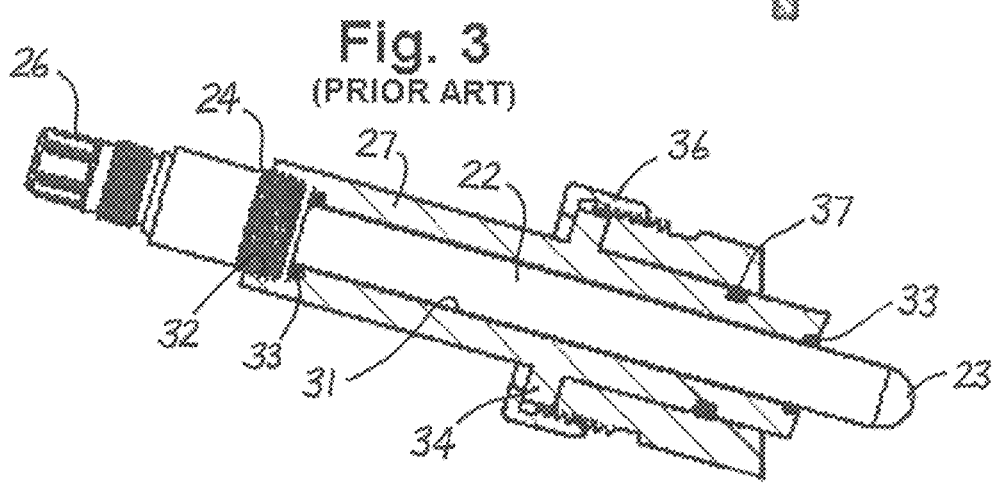
FIG. 3 is a centerline sectional view of the probe installation illustrated in FIG. 2.

In the embodiment illustrated in FIGS. 4-11, the assembly includes a manifold 39 and three probe assemblies 41, with a sampling valve 42, a sampling port 43, and a cleaning port 44.

Each of the probe assemblies includes an electro-chemical probe 21 similar to the one illustrated in FIG. 1 mounted in an adapter sleeve 46. The sleeve has an axially extending bore 47 of slightly greater diameter than the body of the probe, with internal threads 48 at the proximal end of the bore, external threads 49 toward the distal end of the sleeve, and an annular shoulder 50 at the upper end of the external threads. The body of the probe extends through the bore, with the threads on the probe engaging the threads in the sleeve and the tip of the probe extending beyond the distal end of the adapter.

A sealing gasket 51 is mounted on the distal end portion of the probe, with an annular thrust washer 52 between the end of the sleeve and the gasket. The gasket has a generally annular body with a conically inclined, or beveled, sealing surface 53 on one side and an annular lip 54 extending axially from the beveled surface. The gasket is fabricated or molded of a polymer such as an EDPM (ethylene-propylene-diene monomer), a synthetic rubber or rubber composition as, for example, marketed by DuPont under the Viton trademark, or other suitable material. The inner diameter of the gasket is slightly less than the outer diameter of the probe body in order to ensure a tight seal between the probe and the gasket. Thus, for example, with a probe having an outer diameter of 12 mm, for example, the gasket can be manufactured with an inner diameter on the order of 11.9 mm.

The thrust washer has an annular body with flat faces and is fabricated of a material such as polyetheretherketone (PEEK) or polytetrafluoroethylene (PTFE).

The parts are assembled by first inserting the body of the probe into the sleeve and rotating the probe relative to the sleeve to engage the threads to lock the two together. The thrust washer is then slid onto the distal end portion of the probe, and the gasket is slid on after it, with the beveled surface of the gasket facing away from the sleeve and toward the tip of the probe. The gasket and the thrust washer are pushed onto the probe until the thrust washer abuts against the distal end of the sleeve, with the flat side of the gasket against the other side of the washer and the interference fit between the gasket and the probe holding the gasket and the washer in place on the probe.

The body 56 of the manifold has a generally cylindrical side wall 57 and a conically inclined top wall 58, with a standard tri clamp mounting flange 59 extending laterally from the lower portion of the side wall for mating engagement with a similar flange on a connector (not shown) of a type commonly used in connecting valves and other fittings to processing vessels. As is common in tri clamp connectors, flange 59 has an annular sealing surface 61 with an O-ring groove 62 formed therein and an inclined clamping surface 63 opposite the sealing surface for engagement by the tri clamp to urge the two flanges together.

The manifold has a conically shaped chamber 66 which opens through the under side of the manifold body and communicates directly with the interior of a vessel on which the manifold is installed.

Probe ports 67 are formed in the manifold body and extend between top wall 58 and chamber 66. In the embodiment illustrated, three such ports are provided, and they are positioned 60 degrees apart along an arc on one side of the chamber, with sampling port 43 and cleaning port 44 on the other side of the chamber. However, depending upon the application in which the assembly is used, a greater or lesser number of ports can be provided, and they can be positioned as desired.

Each of the probe ports has a bore 68 with a section of reduced diameter 69 at its lower end. The bore is inclined at an angle between about 30 degrees to the horizontal and 30 degrees to the vertical in order to accommodate a variety of probes including ones containing liquids that must remain in contact with the tips of the probes. The upper portion of the bore has internal threads 71 for receiving the external threads of a probe assembly, with an annular shoulder 72 at the upper end of the threads serving as a limiting abutment, or stop, for the probe assembly.

Each of the probe ports also has a seat 73 at the lower end of the bore with a surface 74 for engagement with the beveled face 53 of the probe assembly gasket. The seating surface has an outer frusto-conical section 74a which is inclined at the same angle as the beveled face and an inner frusto-conical section 74b which is inclined at a lesser angle. As illustrated in FIG. 10, the outer section can, for example, be inclined at an angle on the order of 25 degrees to a plane perpendicular to the axis of the bore, with the inner section being inclined at an angle on the order of 15 degrees to that plane. An opening 76 in the seat communicates directly with chamber 66, and the seat is fully exposed for inspection and cleaning when the probe assembly is removed.

Figure 11:
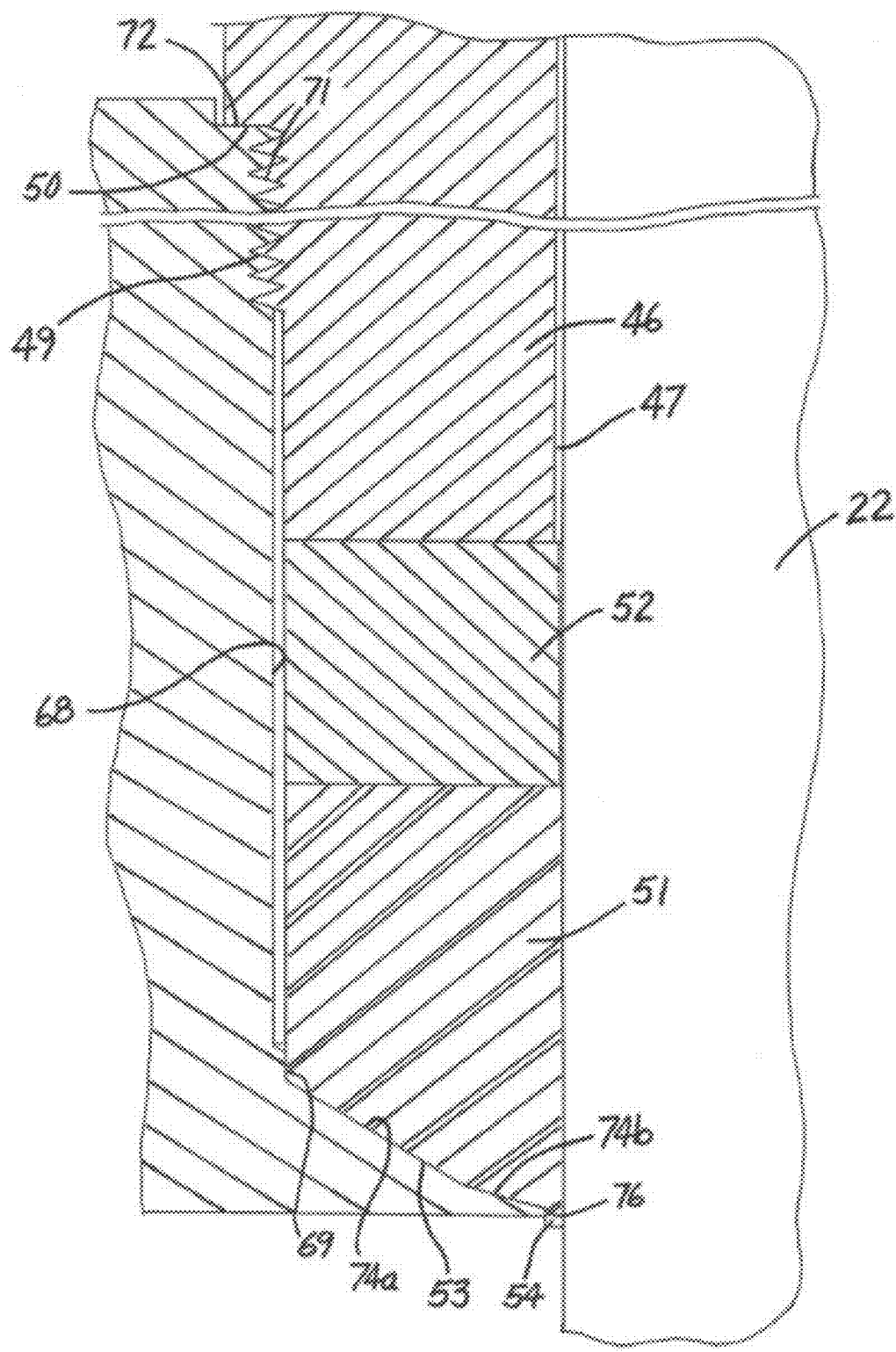
FIG. 11 is an enlarged, fragmentary sectional view of one of the installed probes in the embodiment of FIG. 4, rotated to a vertical position.

As best seen in FIG. 11, a probe assembly in installed in the port by threading the assembly into the port until shoulder 50 abuts against shoulder 72, with the distal end portion of the probe extending into chamber 66. As the probe assembly advances, the beveled face 53 of gasket 51 engages the surface 74 of seat 73, and the gasket is compressed between thrust washer 52 and the seating surface. With the difference in angle between the two sections of the seating surface, the gasket first engages the section of lesser inclination (section 74b), and the portion of the gasket adjacent to that surface is compressed axially to a greater degree than the remainder of the gasket. The axial compression causes the gasket to expand radially against the probe, producing a tighter seal where the seat is less steeply inclined and the radial forces are greater.

The thrust washer isolates the gasket from the twisting motion of the sleeve and protects the gasket from being twisted or damaged during installation and removal of the probe assembly, and the abutment of shoulders 50 and 72 provides a positive stop which controls and limits the degree to which the gasket is compressed. Thus, the integrity of the seal is maintained during probe and/or gasket replacement.

In this particular embodiment, the manifold also includes sampling port 43 and cleaning port 44. These two ports are similar in structure and include radial bores 79 with connector fittings 81, 82 at the outer ends of the bores. The inner ends of the bores communicate directly with an internal chamber 86 that communicates with chamber 66 through a passageway 87. Communication between the chambers is controlled by sampling valve 42 which includes a valve member and actuator of conventional design. The valve member engages a valve seat 88 at the upper end of the passageway, and the actuator is mounted on a tri coupling flange 89 on the upper side of the manifold body and secured to the flange by a tri clamp 91.

Opening the valve provides communication between chamber 66 and sampling port 43, allowing a sample to be drawn from the processing tank. With the valve closed, ports 43, 44, and chamber 86 can be cleaned or sterilized with steam introduced through cleaning port 44.

Figure 12:
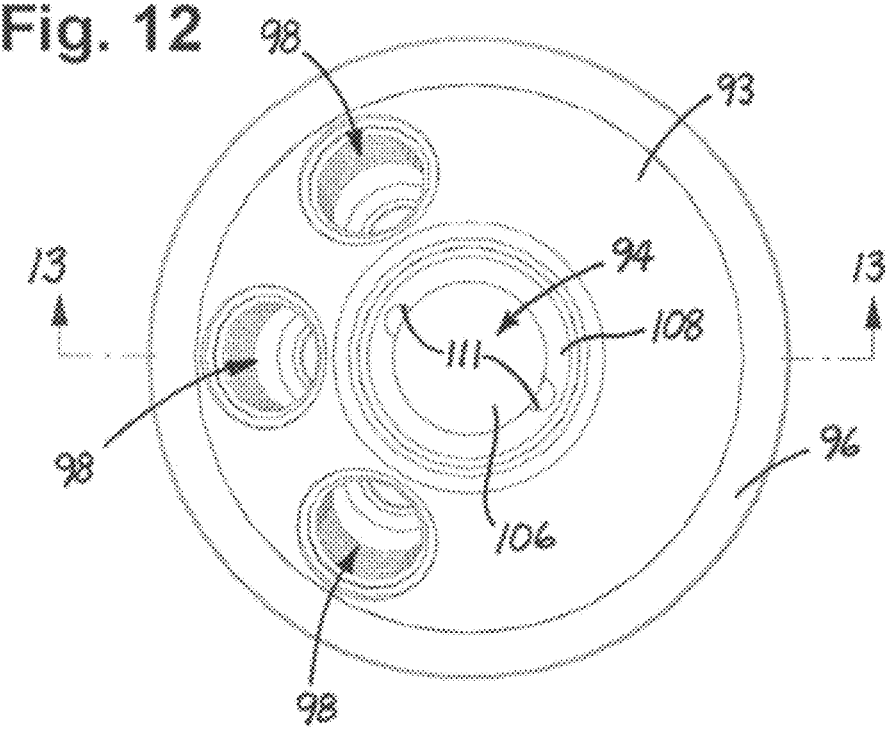
FIG. 12 is a top plan view of another embodiment of a probe manifold according to the invention.
Figure 13:
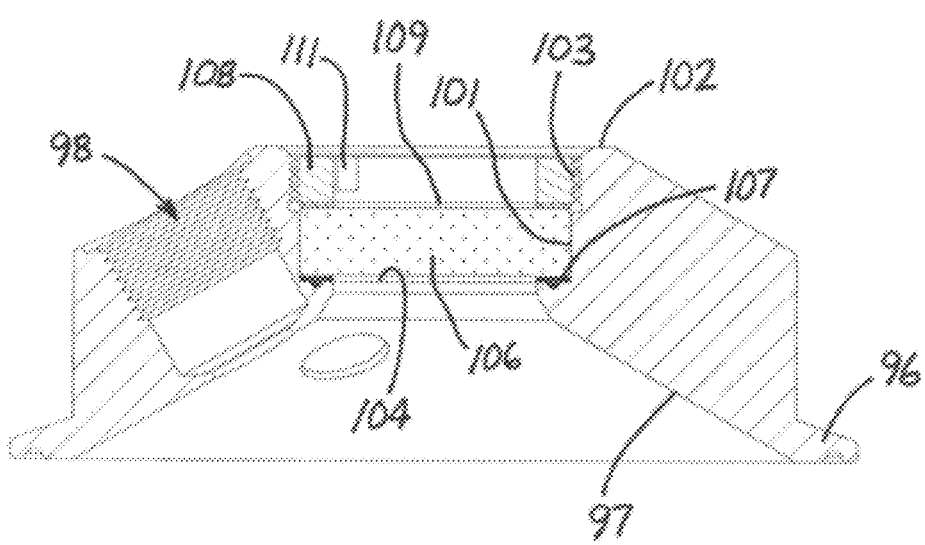
FIG. 13 is a cross-sectional view taken along line 13-13 in FIG. 12.

In the embodiment of FIGS. 12-13, the manifold 93 is similar to manifold 39 except it has a viewing port 94 rather than sampling and cleaning ports and a sampling valve. This manifold has a tri coupling mounting flange 96, a conically-shaped chamber 97, and three probe ports 98 which are substantially identical to the corresponding elements in the embodiment of FIGS. 4-11.

An opening 101 for the viewing port extends between the top wall 102 of the manifold body and chamber 97, with threads 103 toward the upper end of the opening, an annular shoulder 104 toward the lower end, and an O-ring groove in the surface of the shoulder. Between the shoulder and the chamber, the opening flares outwardly to the wall of the chamber. A Pyrex glass window 106 rests on the shoulder, with an annular gasket 107 providing a seal between the glass and the shoulder. The glass is held in place by an externally threaded retaining ring 108 that is threaded into the upper section of the opening and bears downwardly against the glass, with a protective washer 109 between the ring and the glass. The ring has diametrically opposed notches 111 for receiving the lugs of a drive wrench.

The invention has a number of important features and advantages. It permits a plurality of parameters to be monitored with a cluster of probes and a manifold that are readily installed in and removed from a bioprocessing system. The beveled gasket and double-angled seating surfaces produce locally increased radial forces and a tighter seal between the gasket and the probe, and the abutting shoulders of the probe sleeve and manifold provide a positive stop that controls the degree to which the gasket is compressed. The thrust washers protect the gaskets and maintain the integrity of the seals during probe and/or gasket replacement. When the probes are removed from the manifold, the seating surfaces at the lower ends of the ports are exposed for visual inspection and/or cleaning, and since the manifold can also be removed, it is easily inspected and serviced during routine maintenance operations.

It is apparent from the foregoing that a new and improved manifold and probe assembly has been provided. While only certain presently preferred embodiments have been described in detail, as will be apparent to those familiar with the art, certain changes and modifications can be made without departing from the scope of the invention as defined by the following claims.

The invention claimed is:

1. A manifold and probe assembly for a bioprocessing vessel, comprising a manifold having a chamber which communicates with the interior of the vessel and a port which communicates with the chamber, an elongated sensing probe threadedly connected to the port with an end portion of the probe extending into the chamber, a gasket fabricated of a material that expands in one direction when compressed in another having a generally annular body with a conically inclined beveled face mounted on the end portion of the probe, and a seat in the port with a conically inclined surface against which the beveled face is pressed, with the gasket being axially compressed and radially expanded into sealing engagement with the probe.

2. The manifold and probe assembly of claim 1 wherein the seating surface has an outer section which is inclined at the same angle as the beveled face of the gasket and an inner section which is inclined at a lesser angle.

3. The manifold and probe assembly of claim 2 wherein the outer section of the seating surface is inclined at an angle on the order of 25 degrees, and the inner section is inclined at an angle on the order of 15 degrees.

4. The manifold and probe assembly of claim 1 including an adapter sleeve which is threadedly connected to the port, with the probe being threadedly mounted in the adapter sleeve.

5. The manifold and probe assembly of claim 4 including a thrust washer mounted on the distal end portion of the probe between the adapter sleeve and the gasket for protecting the gasket while the sleeve is being connected to the port.

6. The manifold and probe assembly of claim 1 including a stop that limits travel of the probe toward the seat and thereby controls the degree to which the gasket is compressed.

7. The manifold and probe assembly of claim 1 wherein the probe is inclined at an angle between about 30 degrees to the horizontal and 30 degrees to the vertical.

8. The manifold and probe assembly of claim 1 wherein the manifold includes a mounting flange disposed peripherally of the chamber for mating engagement with a similar flange on a connector on the vessel.

9. The manifold and probe assembly of claim 8 wherein the mounting flange has an annular sealing surface and an inclined clamping surface on opposite sides thereof.

10. The manifold and probe assembly of claim 1 wherein the gasket is fabricated of an elastomeric material.

11. The manifold and probe assembly of claim 10 wherein the elastomeric material is chosen from the group consisting of ethylene-propylene-diene monomer, a synthetic rubber, and a rubber composition.

12. A manifold and probe assembly for a bioprocessing vessel, comprising a manifold having a chamber which communicates with the interior of the vessel and a port with a seating surface having inner and outer frusto-conical sections with different angles of inclination surrounding an opening that communicates with the chamber, an adapter sleeve threadedly connected to the port, a sensing probe carried by the adapter sleeve with a distal end portion of the probe extending beyond the distal end of the sleeve, through the opening, and into the chamber, a gasket on the distal end portion of the probe having a generally annular body with a conically inclined beveled face in compressive engagement with the seating surface, a thrust washer on the probe between the distal end of the sleeve and the gasket, and abutting surfaces on the manifold and the adapter sleeve limiting travel of the sleeve and the degree to which the gasket is compressed.

13. The manifold and probe assembly of claim 12 wherein the beveled face of the gasket and the outer section of the seating surface are inclined at similar angles, and the inner section is inclined at a lesser angle.

14. The manifold and probe assembly of claim 13 wherein the beveled face and the outer section are inclined at an angle on the order of 25 degrees, and the inner section is inclined at an angle on the order of 15 degrees.

15. The manifold and probe assembly of claim 12 wherein the port has an axially extending bore with an internal threads toward the outer end of the bore and an annular shoulder at the outer end of the threads, and the adapter sleeve has external threads which mate with the threads in the port and an annular shoulder above the threads which abuts against the shoulder at the outer end of the port.

16. The manifold and probe assembly of claim 12 wherein the probe is inclined at an angle between about 30 degrees to the horizontal and 30 degrees to the vertical.

17. The manifold and probe assembly of claim 12 wherein the manifold includes a mounting flange disposed peripherally of the chamber for mating engagement with a similar flange on a connector on the vessel.

18. A manifold and probe assembly for a bioprocessing vessel, comprising a manifold having a chamber which communicates with the interior of the vessel and a plurality of ports each having a seating surface with inner and outer frusto-conical sections having different angles of inclination surrounding openings that communicate with the chamber, adapter sleeves threadedly connected to the ports, sensing probes carried by the adapter sleeves with distal end portions of the probes extending beyond the distal ends of the sleeves, through the openings, and into the chamber, gaskets on the distal end portions of the probes having generally annular bodies with conically inclined beveled faces engaging the seating surfaces, with the gaskets being compressed axially and expanded radially into sealing engagement with the probe.

19. The manifold and probe assembly of claim 18 wherein the beveled faces of the gaskets and the outer sections of the seating surface are inclined at similar angles, and the inner sections are inclined at lesser angles.

20. The manifold and probe assembly of claim 18 including thrust washers mounted on the distal end portions of the probes between the distal ends of the sleeves and the gaskets for protecting the gaskets while the sleeves are being connected to the ports and the gaskets are being compressed.

21. The manifold and probe assembly of claim 18 including stops that limit travel of the sleeves and control the degree to which the gaskets are compressed.

22. The manifold and probe assembly of claim 18 wherein each of the probes is inclined at an angle between about 30 degrees to the horizontal and 30 degrees to the vertical.

23. The manifold and probe assembly of claim 18 wherein the manifold includes a mounting flange disposed peripherally of the chamber for mating engagement with a similar flange on a connector on the vessel.

24. The manifold and probe assembly of claim 18 wherein the manifold has a central opening which communicates with the chamber, with the ports being spaced about the central opening and communicating with the chamber outside the central opening.

25. The manifold and probe assembly of claim 18 including additional ports which communicate with the chamber and a valve mechanism mounted on the manifold for controlling communication between the additional ports and the chamber.

26. The manifold and probe assembly of claim 18 wherein the manifold includes a viewing port through which the chamber can be observed visually.

* * * * *